(12) United States Patent
Chae et al.

(10) Patent No.: US 12,390,136 B2
(45) Date of Patent: Aug. 19, 2025

(54) INSERTION GUIDE NEEDLE FOR CONTINUOUS BLOOD GLUCOSE MONITORING DEVICE

(71) Applicant: I-SENS, INC., Seoul (KR)

(72) Inventors: Kyung Chul Chae, Seoul (KR); Hyun Ho Choi, Seoul (KR); Goang Yel Ryu, Seoul (KR); Ji Hoon Wang, Seoul (KR); Young Jea Kang, Seoul (KR)

(73) Assignee: I-SENS, INC., Seoul (KR)

( * ) Notice: Subject to any disclaimer, the term of this patent is extended or adjusted under 35 U.S.C. 154(b) by 775 days.

(21) Appl. No.: 17/631,355

(22) PCT Filed: Mar. 18, 2020

(86) PCT No.: PCT/KR2020/003706
§ 371 (c)(1),
(2) Date: Jan. 28, 2022

(87) PCT Pub. No.: WO2021/025258
PCT Pub. Date: Feb. 11, 2021

(65) Prior Publication Data
US 2022/0322981 A1    Oct. 13, 2022

(30) Foreign Application Priority Data
Aug. 7, 2019  (KR) .................. 10-2019-0095972

(51) Int. Cl.
*A61B 5/15*    (2006.01)
*A61B 5/145*   (2006.01)

(52) U.S. Cl.
CPC ...... *A61B 5/15016* (2013.01); *A61B 5/14532* (2013.01)

(58) Field of Classification Search
CPC .............. A61B 5/1411; A61B 5/14503; A61B 5/150396; A61B 2560/063
See application file for complete search history.

(56) References Cited

U.S. PATENT DOCUMENTS

2011/0288574 A1    11/2011  Curry et al.
2016/0058474 A1    3/2016   Peterson et al.
(Continued)

FOREIGN PATENT DOCUMENTS

EP    3 195 891       7/2017
JP    2003-260042     9/2003
(Continued)

OTHER PUBLICATIONS

Extended European Search Report dated Aug. 5, 2024 for European Patent Application No. 24169614.5.
(Continued)

*Primary Examiner* — Eric F Winakur
*Assistant Examiner* — Noah M Healy
(74) *Attorney, Agent, or Firm* — WOMBLE BOND DICKINSON (US) LLP

(57) ABSTRACT

The present disclosure relates to an insertion guide needle for a continuous glucose monitoring system. The insertion guide needle makes an incision in the skin by point-contacting with the skin during a skin insertion process, and allows expanded incision of the skin continuously thereafter. During a process of expanded incision of the skin, the insertion guide needle allows expanded incision continuously and gradually in the width direction and thickness direction. In addition, during the expanded incision process, since the entire incision area is formed by an incision, the insertion guide needle is simply inserted along the incision area after a predetermined insertion section.

9 Claims, 8 Drawing Sheets

(56) References Cited

U.S. PATENT DOCUMENTS

| | | | |
|---|---|---|---|
| 2016/0361091 A1 | 12/2016 | Frey et al. | |
| 2017/0086725 A1 | 3/2017 | Woo et al. | |
| 2017/0274153 A1* | 9/2017 | Ueda | A61M 5/3286 |
| 2019/0038876 A1* | 2/2019 | Isaacson | A61B 17/3415 |
| 2019/0076073 A1 | 3/2019 | Donnay et al. | |

FOREIGN PATENT DOCUMENTS

| | | |
|---|---|---|
| JP | 2016-128031 | 7/2016 |
| JP | 2017-525516 | 9/2017 |
| KR | 10-2017-0045236 | 4/2017 |
| KR | 10-2018-0059519 | 6/2018 |
| KR | 10-2018-0132552 | 12/2018 |
| KR | 10-2019-0025208 | 3/2019 |
| KR | 10-2021-0018630 | 2/2021 |
| WO | 2017/053288 | 3/2017 |
| WO | 2018/166963 | 9/2018 |
| WO | 2018/222009 | 12/2018 |
| WO | 2019/045503 | 3/2019 |
| WO | 2021/025257 | 2/2021 |
| WO | 2021/025258 | 2/2021 |

OTHER PUBLICATIONS

Examination Report No. 1 dated Oct. 6, 2023 for New Zealand Patent Application No. 784489.
International Search Report for PCT/KR2020/003706 mailed on Jul. 2, 2020 and its English translation from WIPO (now published as WO 2021/025257).
Written Opinion of the International Searching Authority for PCT/KR2020/003706 mailed on Jul. 2, 2020 and its English translation by Google Translate (now published as WO 2021/025257).
Office Action for Japanese Patent Application No. 2022-503992 issued on Dec. 13, 2022 and its English translation from Global Dossier.
Examination Report No. 1 dated Oct. 11, 2022 for Australian Patent Application No. 2020325151.
International Preliminary Report on Patentability (Chapter I) for PCT/KR2020/003706 issued on Feb. 8, 2022 and its English translation from WIPO (now published as WO 2021/025257).

* cited by examiner

[Fig. 1]
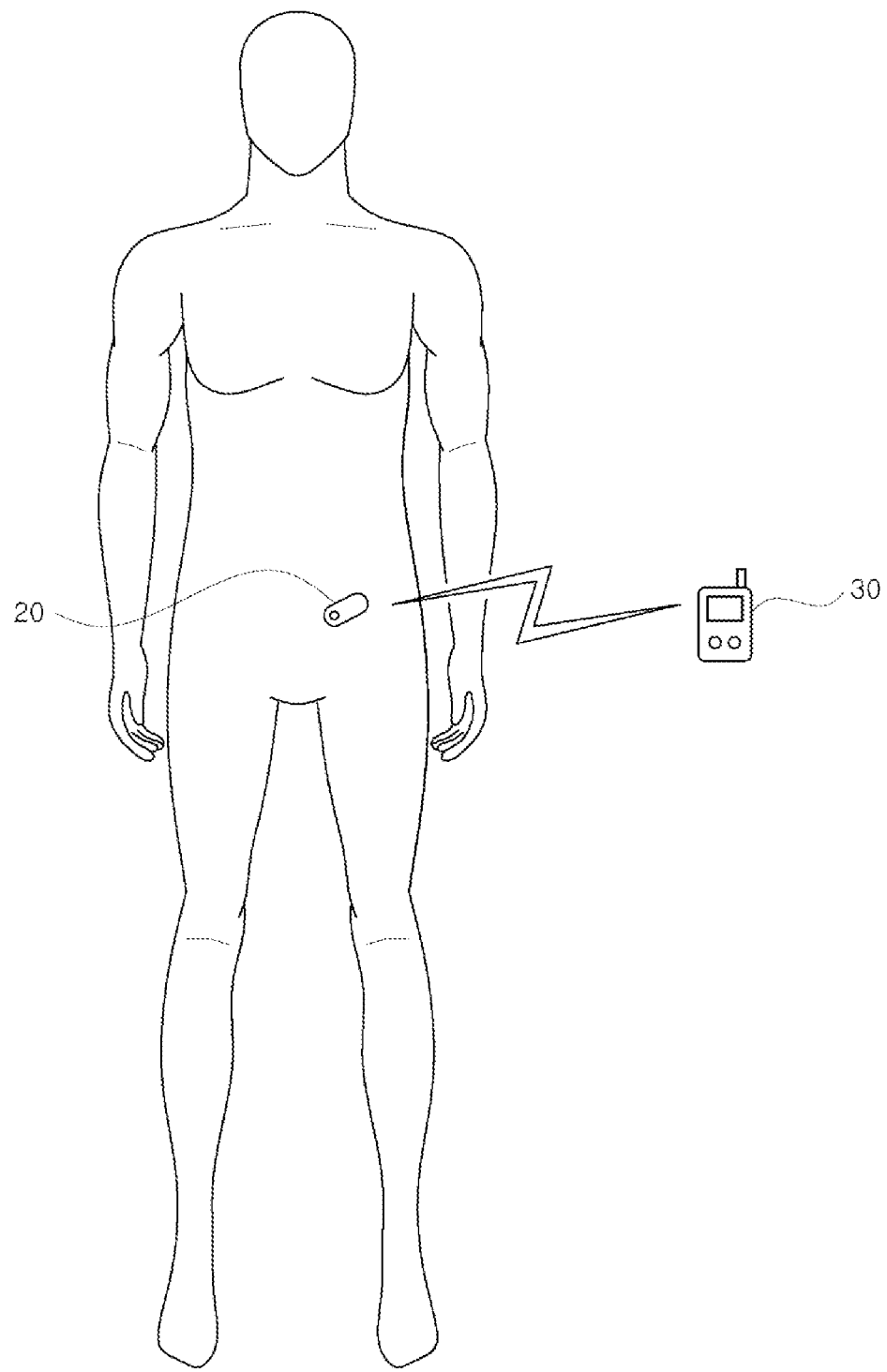

[Fig. 2]
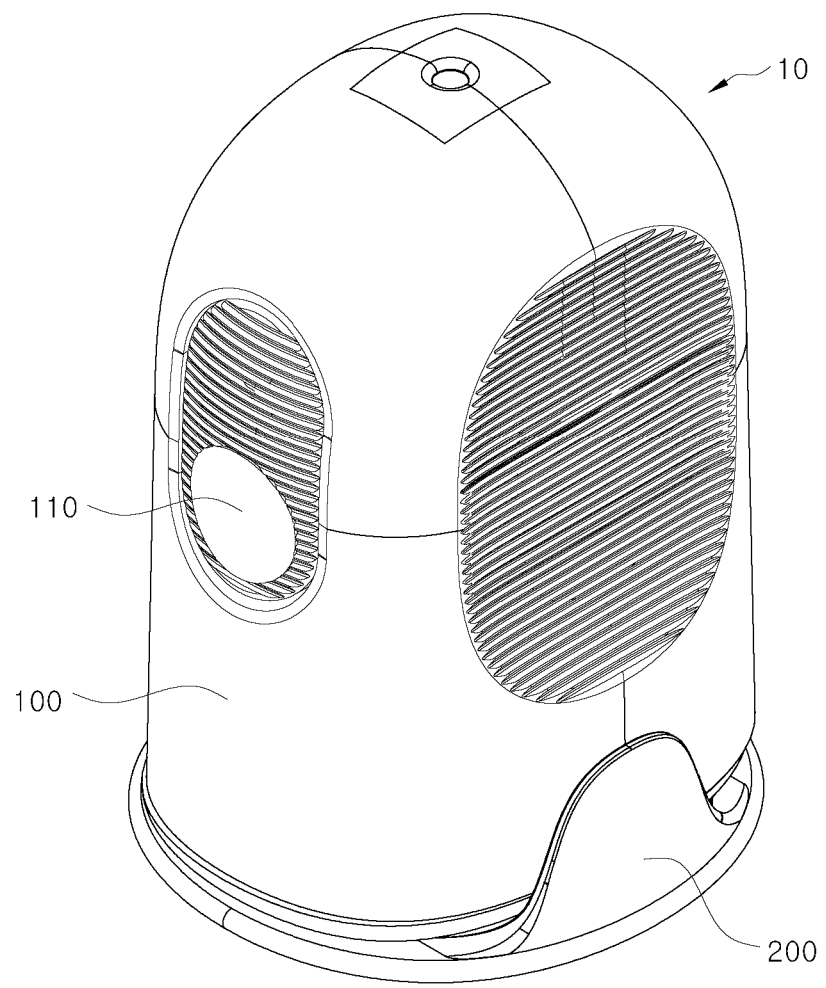

[Fig. 3]
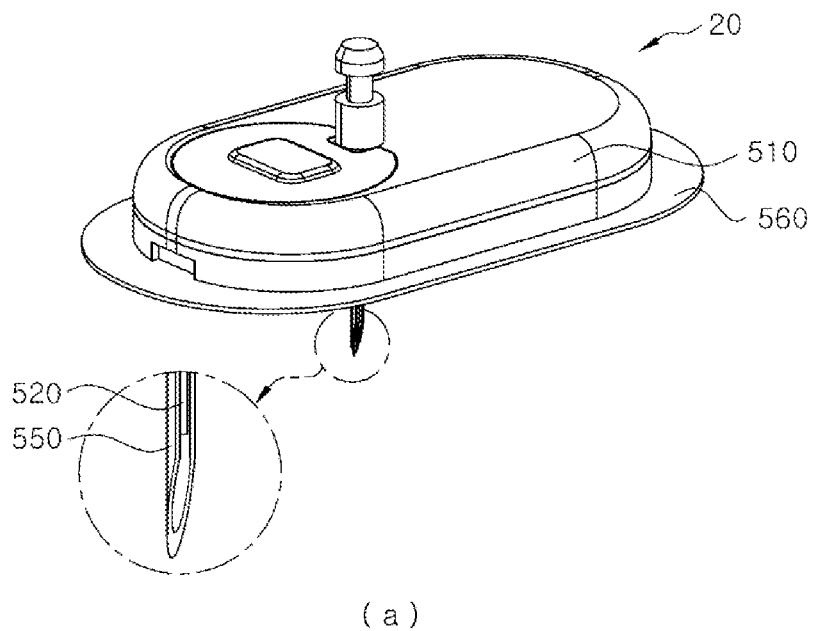
(a)
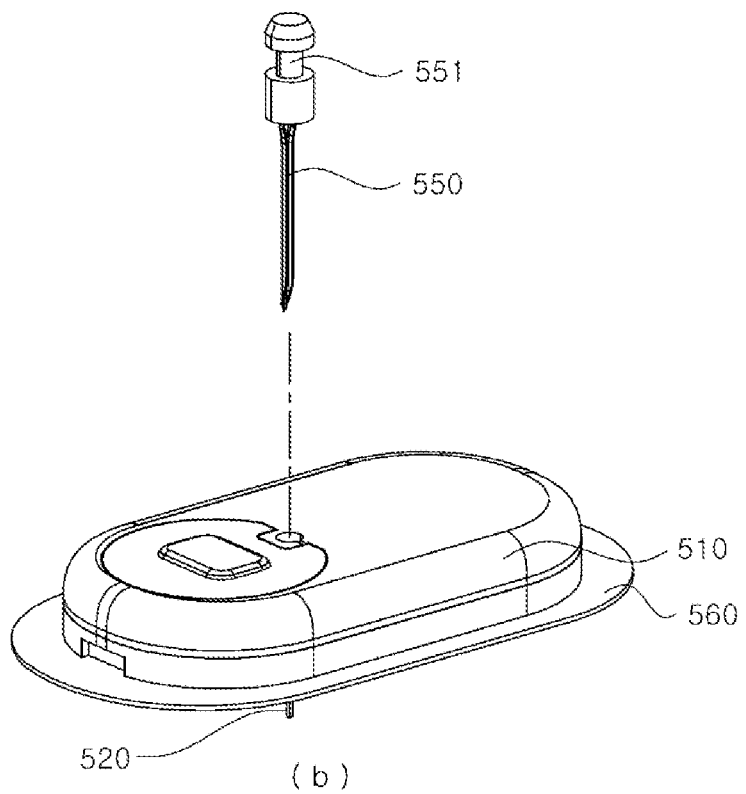
(b)

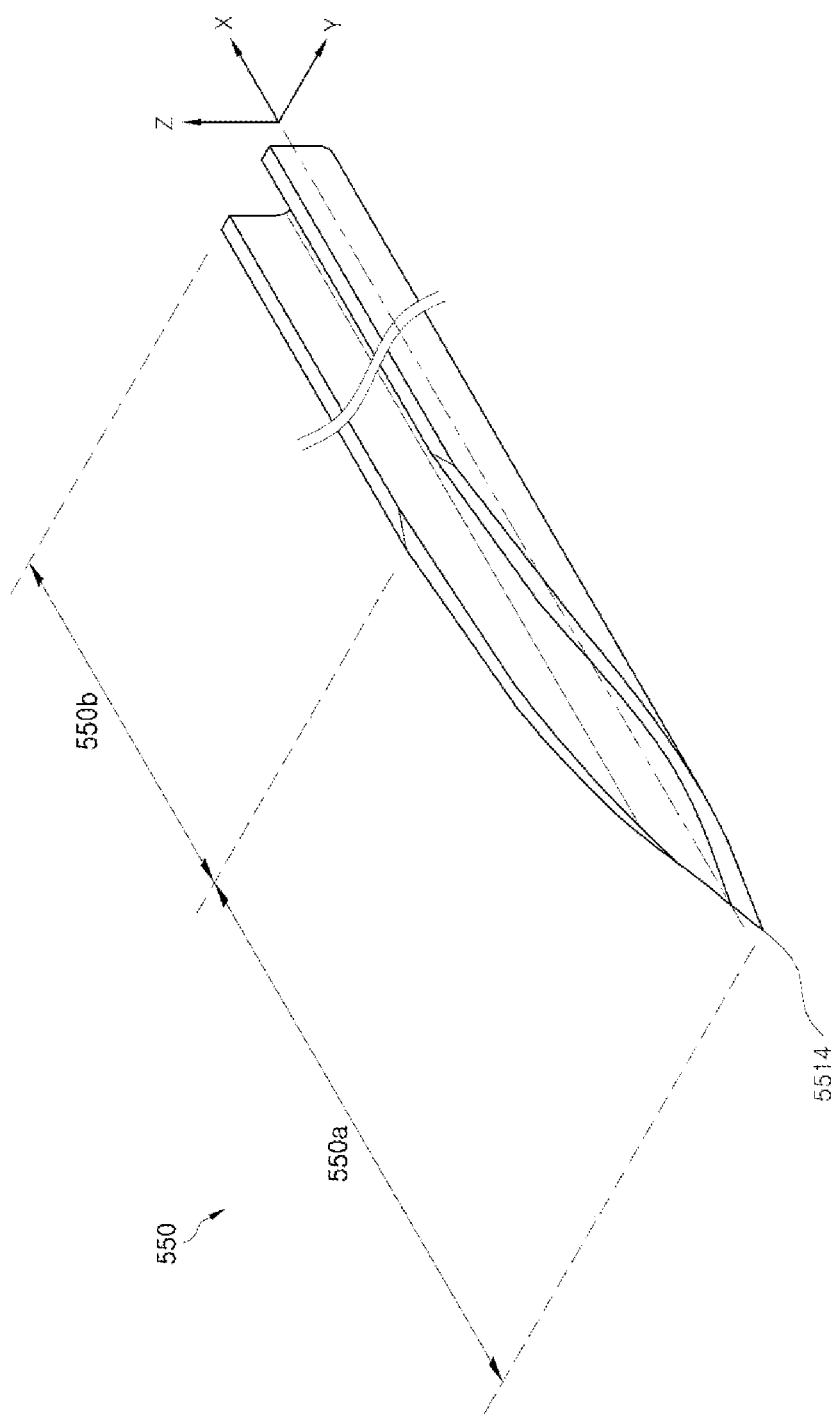
[Fig. 4]

[Fig. 5]
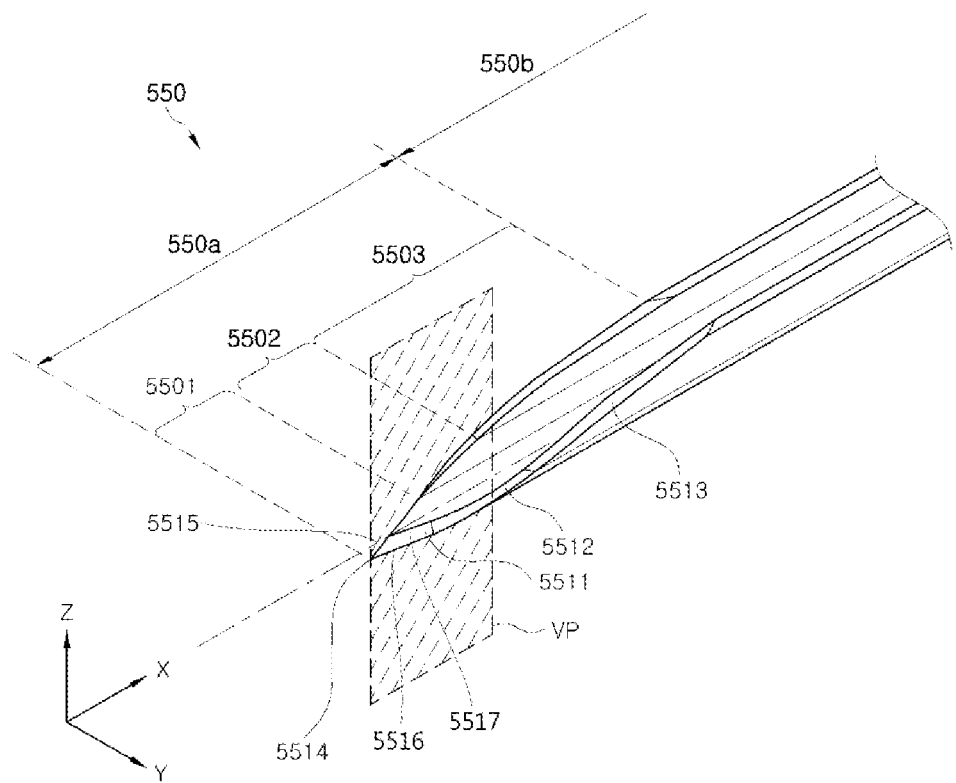
[Fig. 6]
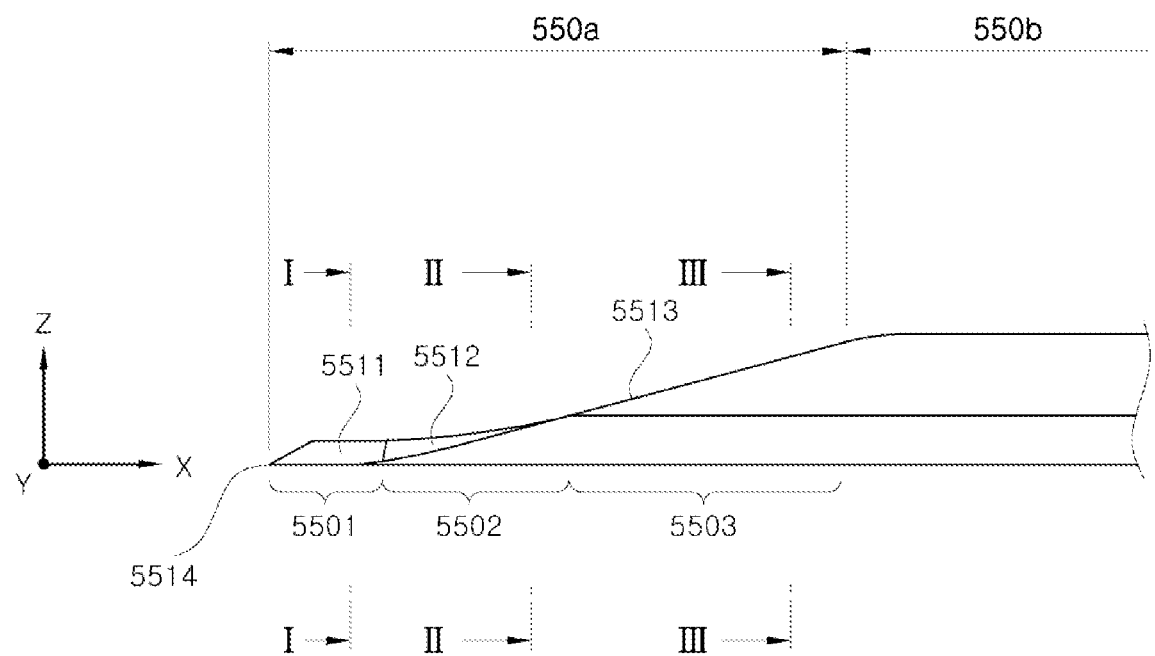

[Fig. 7]
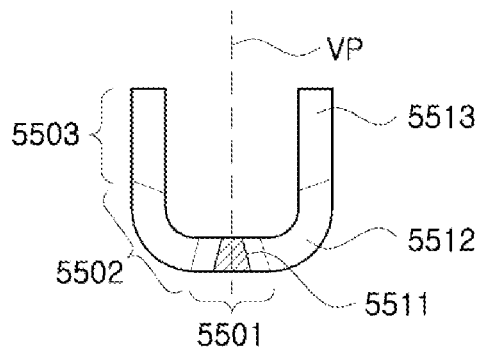
(a) I-I
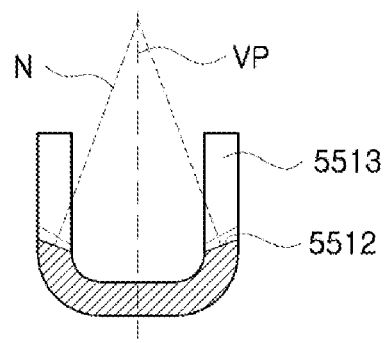
(b) II-II
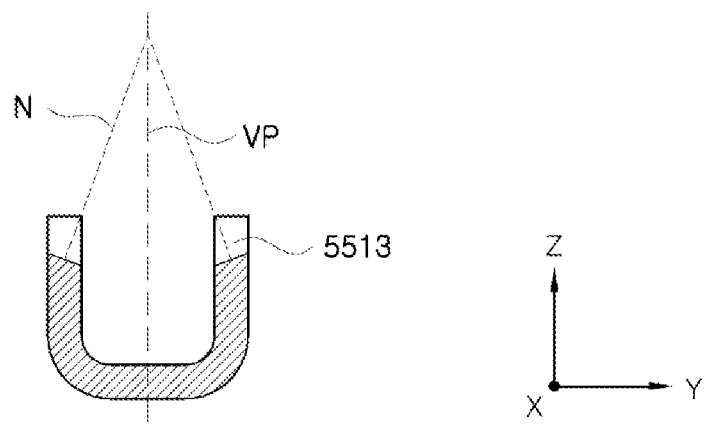
(c) III-III

[Fig. 8]
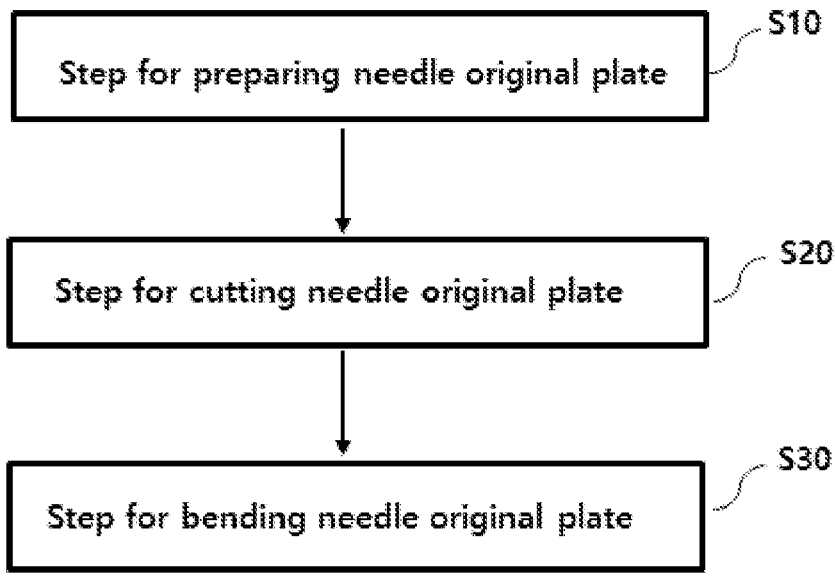
[Fig. 9]
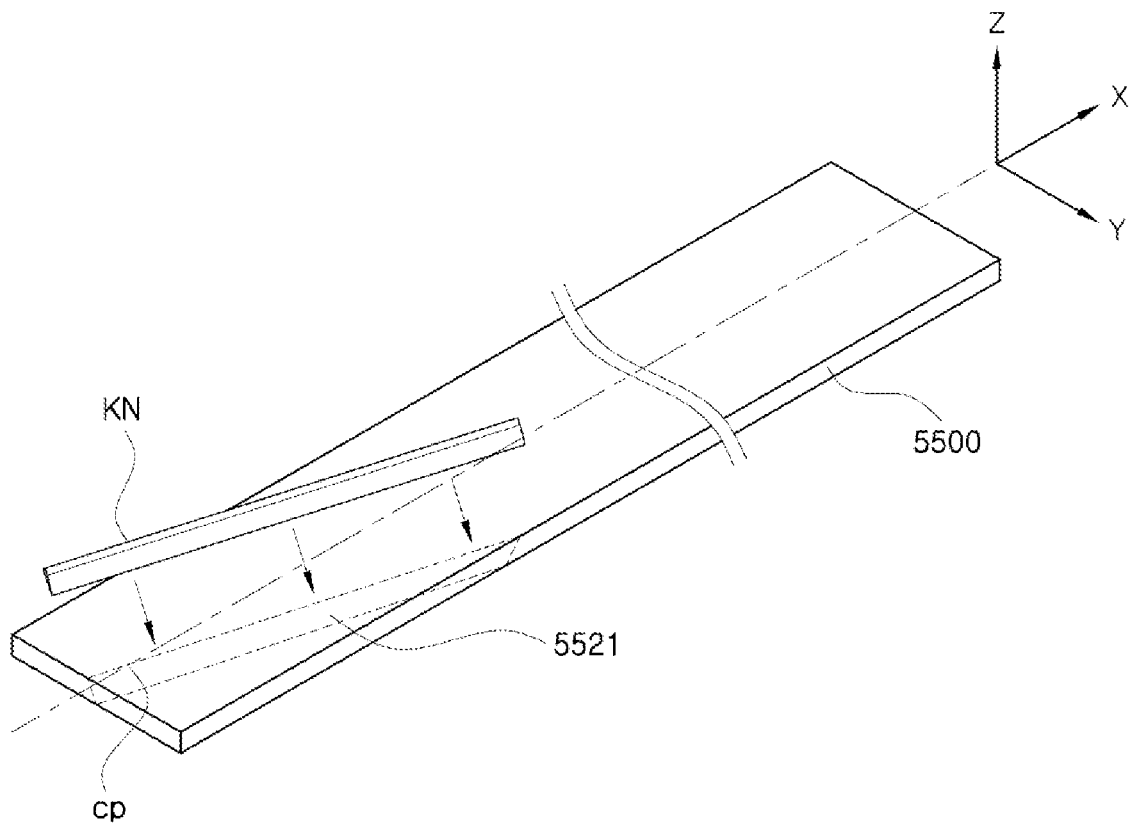

[Fig. 10]
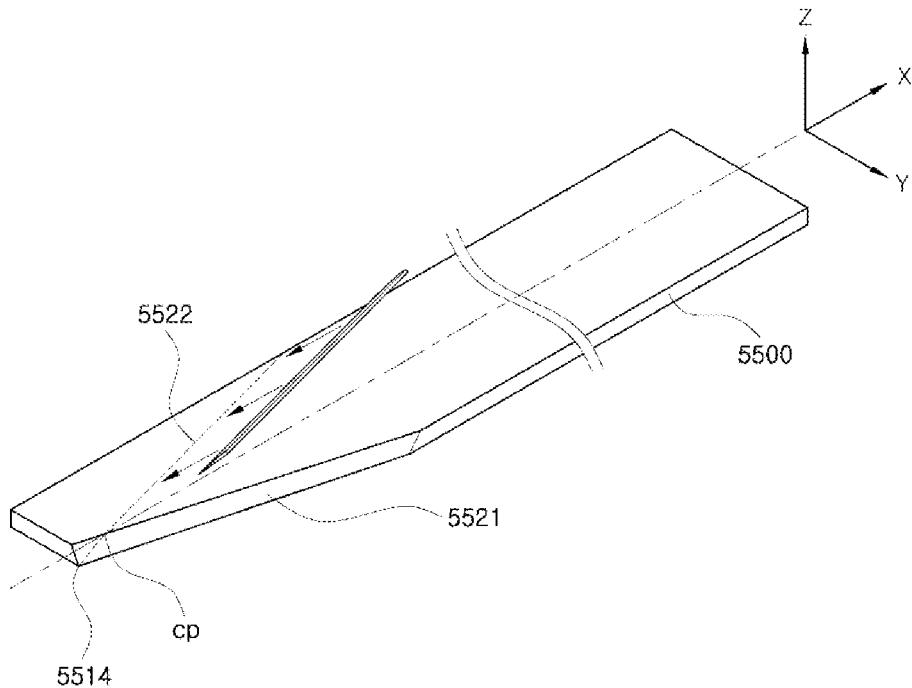
[Fig. 11]
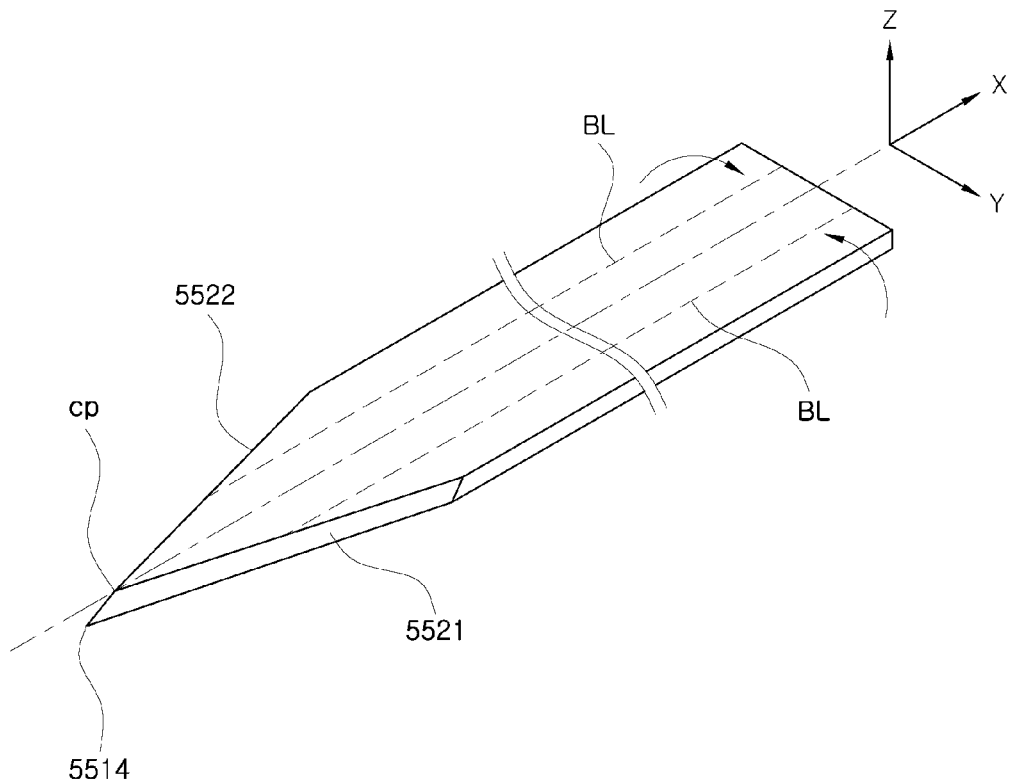

INSERTION GUIDE NEEDLE FOR CONTINUOUS BLOOD GLUCOSE MONITORING DEVICE

CROSS-REFERENCE TO RELATED APPLICATIONS

The present application is the U.S. National Phase of PCT Application No. PCT/KR2020/003706 filed on Mar. 18, 2020, which claims the priority to Korean Patent Application No. 10-2019-0095972 filed on Aug. 7, 2019, the entire contents of which are incorporated herein by reference.

TECHNICAL FIELD

The present disclosure generally relates to an insertion guide needle for a continuous blood glucose monitoring device. In more detail, the present disclosure relates to an insertion guide needle for a continuous blood glucose monitoring device in which, by being capable of incising skin in a type of point-contacting with the skin in a skin insertion process and then continuously enlarging an incised portion of the skin, pain which can be caused by the skin insertion process of the insertion guide needle can be minimized, and therefore repulsion or tension can be relieved when using the continuous blood glucose monitoring device, and by continuously and gradually enlarging the incised portion of the skin in the width direction and the thickness direction during the process of incising the skin and enlarging the incised portion of the skin, skin resistance during the enlargement incision process can be reduced thereby more relieving pain, and because during the enlargement incision process an entire incision area is formed by incision and after a certain insertion area simple insertion is performed along the incision area, almost no pain occurs in this process.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels at home.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

Additionally, the blood-collecting glucose monitoring system performs the glucose measurement by collecting blood by pricking a pain-sensitive fingertip with a needle by the diabetes patients themselves, and therefore, the blood collecting process may cause pain and aversion. To minimize such pain and aversion, research and development regarding the CGMSs, which can continuously measure glucose levels by inserting a needle-shaped sensor into a portion of the human body, such as the belly or an arm, which is less pain sensitive, have been undertaken, and furthermore, research and development of non-invasive glucose monitoring systems for measuring glucose without collecting blood have been actively undertaken.

Over the past 40 years, non-invasive glucose monitoring systems have been studied regarding various methods of measuring glucose without collecting blood, for example, optical methods, electrical methods, exhalation measurement methods, and the like. Cygnus Corporation, Redwoo City, Calif., U.S.A, has developed and launched the Glucowatch® G2 Biographer, a wrist watch type, using reverse iontophoresis, but the sales of this product were stopped in 2007, because of many problems, such as skin stimulation issues and qualification approval issues, malfunction caused by sweating, and low reliability in measurement of hypoglycemia comparing with hyperglycemia. Although a variety of non-invasive glucose monitoring techniques have been introduced and reported to date, there have been no practical uses due to low reliability or accuracy.

A continuous glucose monitoring system includes a sensor module attached to the skin of the human body and measuring a blood glucose level by extracting body fluid, a transmitter transmitting the blood glucose level measured by the sensor module to a terminal, the terminal outputting the received blood glucose level, and any other appropriate component. The sensor module includes a needle-shaped sensor probe for insertion into subcutaneous fat to extract interstitial fluid and any other appropriate component. A separate applicator for attaching the sensor module to the body is used.

Those continuous glucose monitoring systems are manufactured to have a wide variety of types depending on their manufacturers, and are used in a variety of methods. However, the most of the continuous glucose monitoring systems are manufactured and distributed as a type that a one-time use sensor module is attached to the human body using an applicator, and an adhesive tape is attached to an outer housing of the sensor module so that the sensor module can be attached to the human body. If the sensor module is attached to the human body skin through the applicator according to this structure, a state that the sensor module is attached to the human body skin is maintained by the adhesive tape, and, the blood glucose is continuously measured in this state.

Because a portion of the sensor module of the sensor unit inserted into the skin is made of flexible material, an insertion guide needle is included for guiding the sensor unit when the sensor unit is being inserted into the skin. Accordingly, the portion of the sensor unit inserted into the skin is arranged to outwardly protrude from an outside housing bottom surface of the sensor module, the insertion guide needle is arranged to cover an outside of the portion of the sensor unit inserted into the skin, and the insertion guide needle is inserted into the skin together with the sensor unit when the sensor module is attached to the skin through the applicator. If the skin insertion process of the sensor unit is completed, the insertion guide needle is configured to be removed from the skin by the applicator.

In the process of inserting the sensor unit, the insertion guide needle is inserted into the skin, and penetrates and incises the skin, and during the skin insertion process of the insertion guide needle, the skin incision can cause the user to feel pain. By such a pain, the user feels more repulsion is more nervous whenever performing the insertion process of the sensor module.

Unlike general blood-collecting type blood glucose measuring devices, a continuous blood glucose monitoring device needs an operation of newly inserting the sensor unit every period of generally more than one week, and therefore the repulsion caused by the pain is much lower than the blood-collecting type blood glucose measuring device, but when the continuous blood glucose monitoring device is being used for a long time, there is a problem that such a pain can lower use convenience on the whole.

SUMMARY

Technical Problem

The present disclosure is invented to solve problems in conventional technique, and the purpose of the present disclosure is for providing an insertion guide needle for a continuous blood glucose monitoring device in which, by being capable of incising skin in a type of point-contacting with the skin in a skin insertion process and then continuously enlarging an incised portion of the skin, pain which can be caused by the skin insertion process of the insertion guide needle can be minimized, and therefore repulsion or tension can be relieved when using the continuous blood glucose monitoring device.

Another purpose of the present disclosure is for providing an insertion guide needle for a continuous blood glucose monitoring device in which, by continuously and gradually enlarging the incised portion of the skin in the width direction and the thickness direction during the process of incising the skin and enlarging the incised portion of the skin, skin resistance during the enlargement incision process can be reduced thereby more relieving pain, and because during the enlargement incision process an entire incision area is formed by incision and after a certain insertion area simple insertion is performed along the incision area, almost no pain occurs in this process.

Still another purpose of the present disclosure is for providing an insertion guide needle for a continuous blood glucose monitoring device in which, by incising skin through an outer edge line continuously formed from a dot point tip point-contacting with the skin, skin resistance during the skin incision process can be minimized and pain can be more relieved.

Solution to Problem

According to an embodiment of the present disclosure, a insertion guide needle for a continuous blood glucose monitoring device, which is configured to be inserted into a body and measure blood glucose, being inserted into the body together with a sensor unit for the continuous blood glucose monitoring device to guide body insertion of the sensor unit and being extracted and removed from the body after insertion, the insertion guide needle comprises: an enlargement incision part formed at a front end portion of the insertion guide needle to enlarge an incised portion of skin of the body in a process of being inserted into the body; and an insertion support part formed to extend at a back end portion of the enlargement incision part to be continuously inserted into the body along the incised portion enlarged by the enlargement incision part, wherein the enlargement incision part is formed to have a dot point tip of a structure of point-contacting with the skin of the body when a front end portion of the enlargement incision part is being inserted into the body.

In the present embodiment, the insertion support part may be lengthily formed to have a length component along a first axis of a front-back direction parallel to a direction of the body insertion, and may form an inner receivable space and has a structure of including a whole one side opened along a direction of the first axis, wherein, among a second axis of a width direction perpendicular to the first axis and a third axis of a height direction, the one side may cross with the third axis.

Additionally, the enlargement incision part may comprise: a point tip portion configured to enlarge the incised portion of the skin of the body in a direction of the second axis as being from the dot point tip to a back; a connection portion configured to enlarge the incised portion of the skin of the body in the direction of the second axis as being toward the back, wherein a back end of the communication portion is connected with the insertion support part; and a variation portion disposed between the point tip portion and the connection portion to connect between the point tip portion and the connection portion, and configured to enlarge the incised portion of the skin of the body by changing an enlargement incision direction from the direction of the second axis to a direction of the third axis as being toward the back.

Further, the point tip portion may comprise slanted enlargement surfaces formed to be enlarged in the direction of the second axis as being from the dot point tip toward the back, the slanted enlargement surfaces may be formed along the direction of the second axis at both sides with respect to the dot point tip, and the slanted enlargement surfaces may be formed to be slanted in a direction of being away from a virtual plane comprising the dot point tip and the first axis as being toward a bottom.

In addition, a point tip edge line may be formed by crossing the slanted enlargement surfaces formed at the both sides of the dot point tip with each other with respect to the dot point tip, and the point tip edge line may be formed on the virtual plane comprising the dot point tip and the first axis and may be formed to have a structure of upwardly slated as being from the dot point tip to the back.

Additionally, the variation portion may comprise variation extension surfaces forming a same plane as the slanted enlargement surfaces at a front end of the variation extension surfaces and extended in the directions of the second axis and the third axis in a structure of continuously changing a direction of which variation extension surfaces face as being toward the back.

Further, a surface of a back end of the variation extension surfaces may be formed to be slanted in a direction in which a perpendicular upwardly extended from the surface of the back end of the variation extension surfaces is crossed with the virtual plane including the dot point tip and the first axis.

In addition, the connection portion may comprise channel extension surfaces forming a same plane as the variation extension surfaces at a front end of the channel extension surfaces and extended in the direction of the third axis as being toward the back.

Additionally, a whole area of the channel extension surfaces may be formed to be slanted in a direction in which a perpendicular upwardly extended from the whole area of the channel extension surfaces is crossed with the virtual plane including the dot point tip and the first axis.

Further, the insertion support part may be formed in a shape in which both side end portions in a width direction of the insertion support part are upwardly bent with respect to a plate lengthily formed to have a length component along a front-back direction.

Advantageous Effects of Invention

According to an embodiment of the present disclosure, there are technical effects in that, by being capable of incising skin in a type of point-contacting with the skin in a skin insertion process and then continuously enlarging an incised portion of the skin, pain which can be caused by the skin insertion process of the insertion guide needle can be minimized, and therefore repulsion or tension can be relieved when using the continuous blood glucose monitoring device.

Additionally, there are technical effects in that, by continuously and gradually enlarging the incised portion of the skin in the width direction and the thickness direction during the process of incising the skin and enlarging the incised portion of the skin, skin resistance during the enlargement incision process can be reduced thereby more relieving pain, and because during the enlargement incision process an entire incision area is formed by incision and after a certain insertion area simple insertion is performed along the incision area, almost no pain occurs in this process.

Further, there are technical effects in that, by incising skin through an outer edge line continuously formed from a dot point tip point-contacting with the skin, skin resistance during the skin incision process can be minimized and pain can be more relieved.

BRIEF DESCRIPTION OF THE DRAWINGS

FIG. 1 is a figure of schematically illustrating a basic system of a continuous blood glucose monitoring device according to an embodiment of the present disclosure.

FIG. 2 is a figure for schematically illustrating a structure of an applicator of a continuous blood glucose monitoring device according to an embodiment of the present disclosure.

FIG. 3 is a figure of schematically illustrating a configuration of a body attachable unit of a continuous blood glucose monitoring device according to an embodiment of the present disclosure.

FIG. 4 is a figure for schematically illustrating a structure of an insertion guide needle for a continuous blood glucose monitoring device according to an embodiment of the present disclosure.

FIG. 5 is a perspective view of schematically illustrating a structure of an enlargement incision part of an insertion guide needle according to an embodiment of the present disclosure.

FIG. 6 is a side view of schematically illustrating a structure of an enlargement incision part of an insertion guide needle according to an embodiment of the present disclosure.

FIG. 7 is a cross-sectional view taken along line "I-I", line "II-II", and "III-III" of FIG. 6 according to an embodiment of the present disclosure.

FIG. 8 is a flowchart for illustrating a method for manufacturing an insertion guide needle according to operation flow step by step according to an embodiment of the present disclosure.

FIGS. 9 to 11 are figures for illustrating a method for manufacturing an insertion guide needle according to an embodiment of the present disclosure.

DETAILED DESCRIPTION OF EMBODIMENTS

Hereinafter, embodiments of the present disclosure will be described in detail with reference to the accompanying drawings. Throughout this document, reference should be made to the drawings, in which the same reference numerals and symbols will be used to designate the same or like components. Additionally, in the following description of the present disclosure, detailed descriptions of known functions and components incorporated herein will be omitted in the case that the subject matter of the present disclosure may be rendered unclear thereby.

FIG. 1 is a figure of schematically illustrating a basic system of a continuous blood glucose monitoring device according to an embodiment of the present disclosure, FIG. 2 is a figure for schematically illustrating a structure of an applicator of a continuous blood glucose monitoring device according to an embodiment of the present disclosure, and FIG. 3 is a figure of schematically illustrating a configuration of a body attachable unit of a continuous blood glucose monitoring device according to an embodiment of the present disclosure.

A continuous blood glucose monitoring device according to an embodiment of the present disclosure is configured that a body attachable unit (20) including a sensor unit (520) inserted into the human body for continuous blood glucose measurement is configured to be attached to the human body through an applicator (10), the blood glucose can be continuously monitored by insertedly attaching the body attachable unit (20) to the human body by manipulating the applicator (10), and blood glucose information periodically measured by the body attachable unit (20) is transmitted to a terminal (30) to display it.

A continuous blood glucose monitoring apparatus may be manufactured as one single unit product by assembling a body attachable unit (20) into the inside of an applicator (10), and has a simpler structure which can be easily used by minimizing additional work of a user when using the continuous blood glucose monitoring apparatus.

The body attachable unit (20) may be configured to be attachable to a human body to periodically measure blood sugar level or glucose by extracting body fluid, and transmit the blood glucose measurement result to an external device such as an external terminal (30) and so on. A sensor unit (520) of which one end portion can be inserted into the human body and a wireless communication chip configured to wirelessly communicate with the external terminal (30) can be disposed inside the body attachable unit (20), and therefore, the body attachable unit (20) can be used without additional connection of a separate transmitter.

The applicator (10) is formed such that the body attachable unit (20) is fixedly coupled to inside of the applicator (10), and the applicator (10) is configured to outwardly discharge the body attachable unit (20) according to the manipulation of the user.

In this embodiment, the body attachable unit (20) is assembled and produced in a state that the body attachable unit (20) is inserted into the inside of the applicator (10), and is configured to move in an outward discharge direction pursuant to the operation of the applicator (10) by the manipulation of the user and be attached to the human body.

Therefore, the sensor applicator assembly according to an embodiment of the present disclosure is assembled and manufactured in a state that the body attachable unit (20) is inserted in the inside of the applicator (10) at the manufacturing stage and the body attachable unit (20) can be attached to a skin by only the operation of the applicator (10), and because the sensor applicator assembly (1) is supplied to the user in this state, the user can easily attach the body attachable unit (20) to the skin by only the manipulation simply activating the applicator (10) without extra additional operation for attaching the body attachable unit (20) to the skin. Specifically, since the body attachable unit (20) has the wireless communication chip (540), no connection with an extra transmitter is needed and therefore it can be used more conveniently.

In a conventional continuous blood glucose measurement apparatus, after removing a body attachable unit, which is separately packaged, precisely inserting it into an applicator, and then operating the applicator, the body attachable unit is attached to a skin, but the work precisely inserting the body attachable unit into the applicator is cumbersome as well as difficult and there is a problem in lowering the accuracy of blood glucose measurement because of contaminating the body attachable unit when young children or elderly adults perform this procedure.

In an embodiment of the present disclosure, at the manufacturing stage, it is manufactured and distributed in a state that the body attachable unit (20) is inserted in the applicator (10), and therefore the step that the user removes the body attachable unit (20) from the package and inserts it into the applicator (10) may be omitted, because the body attachable unit (20) can be attached to the skin by simply manipulating the applicator (10), the usability may be significantly improved, and specifically, the accuracy of blood glucose measurement may be improved by preventing the contamination of the body attachable unit (20).

A separate and additional protection cap (200) can be separably coupled to the applicator (10) in order to block external exposure in a state that the applicator (10) is inserted in the inside of the applicator (10), and it may be configured that the user can attach the body attachable unit (20) to the human body by manipulating the applicator (10) only after the protection cap (200) is separated.

In the embodiment of the present disclosure, an adhesive tape (560) is provided at a side of the body attachable unit (20) contacting the human body to be attached to the human body, to protect the adhesive tape (560), a release paper (not shown) is attached to a surface of the adhesive tape (560) contacting the human body, and the release paper of the adhesive tape (560) may be configured to be separated and removed from the adhesive tape (560) during the operation of separating the protection cap (200) from the applicator (10).

For example, the release paper of the adhesive tape (560) may be configured to adhere one side of the release paper to the protection cap (200), and therefore, if the user separates the protection cap (200) from the applicator (10), the release paper (560) may be separated and removed from the adhesive tape (560) together with the protection cap (200). Accordingly, if the user separates the protection cap (200), the release paper of the adhesive tape (560) is separated and removed, and therefore in this status the body attachable unit (20) can be attached to the human body by the operation of the applicator (10).

Additionally, in a state that the body attachable unit (20) is inserted in the inside, the applicator (10) fixes the body the attachable unit (20), and in a state that the body attachable unit (20) is outwardly discharged and moved, the applicator (10) is configured to release the fixed state of the body attachable unit (20). Accordingly, in a state that the body attachable unit (20) is assembled to be inserted in the inside of the applicator (10), the body attachable unit (20) maintains the fixed state, and when the body attachable unit (20) is externally discharged and attached to the skin by actuating the applicator (10), the state fixed between the applicator (10) and the body attachable unit (20) is released, and therefore if the applicator (10) is separated in this state the applicator (10) is separated from the body attachable unit (20) and only the body attachable unit (20) remains on the skin.

Meanwhile, the body attachable unit (20) according to an embodiment of the present disclosure is configured to cause the sensor unit (520) and the wireless communication chip to initiate their operations through a separate switching means controlled by the user. Accordingly, after inserting and attaching the body attachable unit (20) to the human body by using the applicator (10), the user may initiate to operate the body attachable unit (20) through the switching means or other appropriate means included in the body attachable unit (20), and from the time of the initiation of the operation the sensor unit (520) and the wireless communication chip may be operated, the blood glucose of the human body may be measured, and the measurement result may be transmitted to the external terminal. In this embodiment, the switching means operated by the user may be implemented in various ways.

Additionally, in the body attachable unit (20), the sensor unit (520) is disposed in a housing (510), and one end portion of the sensor unit (520) outwardly protrudes from the housing (510) so that it can be inserted and attached to the human body. The sensor unit (520) may comprise a sensor probe unit to be inserted into the human body, and a sensor body unit disposed inside the housing (510), and the sensor probe and the sensor body unit are formed as one end portion and another end portion of the sensor unit (520), respectively, and in a bent shape.

In this embodiment, in order to smoothly perform the body insertion process of the sensor unit (520), an insertion guide needle (550) may be separatably coupled to the housing (510). The insertion guide needle (550) may surround one end portion of the sensor unit (520) and be configured to be inserted together with the sensor unit (520) into the human body so that one end portion of the sensor unit (520) can be stably inserted into the human body.

As shown in FIG. 3, the insertion guide needle (550) may be separatably coupled to the housing (510) in a direction penetrating the top and bottom of the housing (510) of the body attachable unit (20), the insertion guide needle (550) may be formed to have a structure covering the outside of the sensor unit (520), and a need head (551) is formed at the upper end portion of the needle unit (550). If the body attachable unit (20) is moved in the direction outwardly discharged by the applicator (10), the insertion guide needle (550) is inserted into the human body first before the sensor unit (520) is inserted into the human body and the insertion guide needle (550) may support the sensor unit (520) such that the sensor unit (520) can be stably inserted in the skin. The insertion guide needle (550) may be coupled with a needle extracting body (not shown) of the applicator (10) through the needle head (551), and after the body attachable unit (20) is inserted and attached to the human body by the operation of the applicator (10), the insertion guide needle (550) may be configured to be withdrew and removed from the human body by the needle extracting body of the applicator (10).

Because the insertion guide needle (550) is inserted into the skin of the human body together with the sensor unit (520), the process of inserting the insertion guide needle (550) into the skin may cause the user to feel pain. The insertion guide needle (550) according to an embodiment of the present disclosure may be configured to have a structure for minimizing pain during the skin insertion process, by during the process of inserting the insertion guide needle (550). The insertion guide needle (550) according to an embodiment of the present disclosure can start to enlarge a skin incision portion from a point area during the process of being inserted into the skin as well as perform continuous enlargement incision simultaneously, thereby being configured to have a structure which can minimize pain during the skin insertion process.

Hereinafter, specific configuration of the insertion guide needle (550) according to an embodiment of the present disclosure will be described in further detail.

FIG. 4 is a figure for schematically illustrating a structure of an insertion guide needle for a continuous blood glucose monitoring device according to an embodiment of the present disclosure, FIG. 5 is a perspective view of schematically illustrating a structure of an enlargement incision part of an insertion guide needle according to an embodiment of the present disclosure, FIG. 6 is a side view of schematically illustrating a structure of an enlargement incision part of an insertion guide needle according to an embodiment of the present disclosure, and FIG. 7 is a cross-sectional view taken along line "I-I", line "II-II", and "III-III" of FIG. 6 according to an embodiment of the present disclosure.

The insertion guide needle (550) according to an embodiment of the present disclosure may be formed to lengthily extend along an insertion direction to be inserted into the human body together with the sensor unit (520), and configured to comprise an enlargement incision part (550a) formed at a front end portion or a portion adjacent to the frontend portion, and an insertion support part (550b) formed to extend at a back end portion of the enlargement incision part (550a).

The enlargement incision part (550a) is formed to incise the skin of the human body and enlarge the incised portion during the process of inserting the insertion guide needle (550), and the insertion support part (550b) is continuously inserted into the human body along the portion incised and enlarged by the enlargement incision part (550a). The enlargement incision part (550a) and insertion support part (550b) can be formed to cover an outer side of a portion of the sensor unit (520) inserted into the human body.

According to such a structure, when the body attachable unit (20) is discharged in a direction of being attached into the human body through the applicator (10), the insertion guide needle (550) coupled to the body attachable unit (20) is inserted into the skin of the human body, and during this process, the enlargement incision part (550a) is inserted first and then the insertion support part (550b) is continuously inserted. When the enlargement incision part (550a) is inserted into the human skin, the skin is incised, as the insertion process is progressing, the incised portion is being enlarged, and after the insertion of the enlargement incision part (550a) is completed, the insertion support part (550h) is inserted along the portion incised by the enlargement incision part (550a). In this process, the enlargement of the incised portion is not occurred by the insertion support part (550h). The sensor unit (520) is arranged in an inside space of the insertion guide needle (550), and is inserted into the human body together with the insertion guide needle (550).

In this embodiment, the enlargement incision part (550a) is formed to have a dot point tip (5514) having a structure for point-contacting with the skin of the human body during the process of inserting the front end of the enlargement incision part (550a) into the human body.

Like this, by forming the front end of the enlargement incision part (550a) as a dot point tip (5514) structure, the enlargement incision part (550a) is point-contacted with the skin when the enlargement incision part (550a) is being inserted into the skin, and therefore an incision start portion of the skin is formed to be very tiny as a dot point, thereby minimizing pain caused by the skin incision.

When the enlargement incision part (550a) is being inserted into the skin, such a enlargement incision part (550a) is configured to enlarge the incised portion around the center of a point where the dot point tip (5514) is disposed, and the detailed description will be provided as follows.

The insertion support part (550b) is formed to extend from the back portion of the enlargement incision part (550a), the insertion support part (550b) is lengthily formed to have a length component along a first axis (hereinafter "X axis") of a front-back direction which is parallel to an insertion direction, and, one surface of the insertion support part (550b) crossing the Z axis, among a second axis (hereinafter "Y axis") of an width direction and a third axis (hereinafter "Z axis") of a height direction which are perpendicular to the X-axis, has an open shape of an whole section along the X axis to form an inner receivable space.

The insertion support part (550b) is formed to have a plate lengthily formed to have a lengthy component along the front-back direction (hereinafter "X axis direction") and having a " ⌐ " shape channel structure of which both end side portions with respect to an width direction are upwardly bent. The shape of the insertion support part (550b) may be formed in a structure of forming an opening at an outer circumferential surface of a tube hollow in a length direction, and may be formed to be open at one side, have a receivable space inside, and be lengthily extended in the X axis direction.

The insertion support part (550*b*) has a structure to accommodate the sensor unit (520) its inside space to surround the outside of the sensor unit (520), and can be inserted into the skin together with the sensor unit (520) along the portion incised by the enlargement incision part (550*a*).

The enlargement incision part (550*a*) of the insertion guide needle (550) will be described in further detail. When the enlargement incision part (550*a*) is being inserted into the skin, the enlargement incision part (550*a*) is configured to gradually and continuously enlarge a skin incision portion from a portion where the dot point tip (5514) is disposed.

For example, the enlargement incision part (550*a*) is configured to include a point tip portion (5501) configured to incise the skin of the human body and enlarge the incised portion along the Y axis direction as being moved from the dot point (5514) to the back, a connection portion (5503) configured to incise the skin of the human body and enlarge the incised portion along the Z axis direction as being moved to the back, wherein the back end of the connection portion (5503) is connected to the insertion support part (550*b*), and a variation portion (5502) disposed between the point tip portion (5501) and the connection portion (5503) to connect the point tip portion (5501) and the connection portion (5503) and configured to incise the skin of the human body and enlarge the incised portion in a direction which is changed from the Y axis direction to the Z axis direction as being moved to the back.

Accordingly, the enlargement incision part (550*a*) incises the skin of the human body and continuously enlarges the incised portion in the Y axis direction from the dot point tip (5514) through the point tip portion (5501) section, then continuously incises and enlarges the skin by changing the enlargement incise direction from the Y axis direction to the Z axis direction through the variation portion (5502) section, and, after that, continuously incises the skin and enlarges the incised portion in the Z axis direction through the connection portion (5503) section.

According to such a structure, during the process in which the enlargement incision part (550*a*) is being inserted into the skin, by point-contacting with the skin through the dot point tip (5514) and starting the operation of skin incision, penetration resistance during the skin incision can be relatively minimized, thereby minimizing the cause of the skin pain, and, after that, by performing a continuous enlargement incision process, specially performing an enlargement incision process continuously and sequentially in the width direction (Y axis direction) and the height direction (Z axis direction), frictional resistance which can occur during the enlargement incision process can be minimized, thereby minimizing the cause of the skin pain during the enlargement incision process.

Slanted enlargement surfaces (5511) are formed to be enlarged from the dot point tip (5514) to the back in the Y axis direction at the point tip portion (5501), and the slanted enlargement surfaces (5511) are formed at both sides with respect to the dot point tip (5514) as a center along the Y axis direction, and is formed to be slated in a direction away from the dot point tip (5514) and a virtual plane (VP) including the X axis as being down to the bottom.

An outside edge line (5516) of the slanted enlargement surfaces (5511) is connected with the dot point tip (5514), accordingly the outside edge line (5516) being enlarged from the dot point tip (5514) toward the back in the Y axis direction is formed to be connected with the dot point tip (5514), and the point tip portion (5501) incises the skin and enlarges the incised portion along the Y axis direction along the outside edge line (5516).

Additionally, the slanted enlargement surfaces (5511) formed at both sides of the dot point tip (5514) forms a point tip edge line (5515) by crossing each other at the dot point tip (5514) as the center, and the point tip edge line (5515) is formed on the virtual plane (VP) comprising the dot point tip (5514) and the X axis and is formed in the structure of being upwardly slated as being from the dot point tip (5514) toward the back.

The point tip edge line (5515) is formed at a thickness side of the point tip portion (5501), and therefore, by the point tip portion (5501), the skin is minutely incised and the incised portion is enlarged in the Z axis direction at a section corresponding to the thickness of the point tip portion (5501) through the point tip edge line (5515).

At the upper portion of the point tip edge line (5515), an inside edge line (5517) is formed to be enlarged in the Y axis direction from the upper portion of the point tip edge line (5515) to the back. Therefore, by forming the slanted enlargement surface (5511) in a structure of a slated cut surface, the inside edge line (5517) and the outside edge line (5516) are formed at the upper portion and the lower portion of the slanted enlargement surface (5511), respectively, and the process of the skin enlargement incision is mainly performed through the outside edge line (5516) located at the outside in the Y axis direction. At that time, depending on the user's need, the inside edge line (5517) can be formed in a curved surface structure without an edge by a grinding operation. Accordingly, the inside edge line (5517) can be formed in a structure of side-contacting the skin, not line-contacting the skin.

According to such a structure, the point tip portion (5501) of the enlargement incision part (550*a*) incises the skin and enlarges the incised portion in the Y axis direction by the outside edge line (5516) by forming the outside edge line (5516) from the dot point tip (5514) point-contacting the skin toward both sides of the Y axis direction, and incises the skin and enlarges the incised portion in the Z axis direction as much as a thickness section by forming the point tip edge line (5515) in the Z axis direction at the thickness section.

Because the skin is incised and the incised portion is enlarged in multiple directions from the dot point tip (5514), skin resistance during the incision start process by the dot point tip (5514) and the enlargement incision process by the edge lines (5515, 5517) can be minimized, and therefore the skin pain during the incision process can be minimized.

The variation portion (5502) is formed at the back portion of the point tip portion (5501), and a variation extension surface (5512) forming the same plane as the slanted enlargement surface (5511) at the front end portion and extending in the Y axis and Z axis directions in a structure of continuously changing a direction of facing a side as being toward the back is formed at the variation portion (5502).

A surface of the back end portion of the variation extension surface (5512) is formed to be slanted in a direction in which a perpendicular (N) upwardly extended from the surface is crossed with the virtual plane (VP) including the dot point tip (5514) and the X axis.

Accordingly, the variation extension surface (5512) is formed in a structure of starting from the back end of the slated enlargement surface (5501) of the point tip portion (5501) extended in the Y axis direction and being continuously changed in the Y axis and Z axis directions, the inside edge line (5517) and the outside edge line (5516) of the variation extension surface (5512) are formed to be continuously formed with the inside edge line (5517) and the outside edge line (5516) of the slated enlargement surface (5511). In addition, because the perpendicular (N) is crossed with the virtual plane (VP) on the back surface of the variation extension surface (5512), the surface direction of facing at the back surface of the variation extension surface (5512) is formed in a way of being slanted toward the inside center. According to the surface shape, at an insertion section along the surface shape after the variation portion (55925502), an outmost insertion incision portion is determined by an outside edge line (5516) in the Y axis and Z axis directions.

The connection portion (5503) is formed at the back end of the variation unit portion (5502), and a channel extension surface (5513) forming the same plane as the variation extension surface (5512) of the variation portion (5502) at the front end of the connection portion (5503) and being extended in the Z axis direction toward the back of the connection portion (5503) is formed at the connection portion (5503).

The channel extension surface (5513) is formed to be slanted in a direction in which the perpendicular (N) upwardly extending from the surface is crossed with the virtual plane (VP) including the dot point tip (5514) and the X axis. Accordingly, the direction of a surface at a back end surface of the channel extension surface (5513) is formed in a structure of being slated toward the inside center, and, at the insertion section after the connection portion (5503), an outmost insertion incision portion is determined by the outside edge line (5516). Accordingly, the insertion support part (550*b*) inserted after that is inserted along the portion incised by the outside edge line (5516).

According to such a structure, after the enlargement incision part (550*a*) incises the skin and enlarges the incised portion along the Y axis direction by the slanted enlargement surface (5511) at the point tip portion (5501), the enlargement incision part (550*a*) changes an enlargement incision direction from the Y axis direction to the Z axis direction by the variation extension surface (5512) at the variation portion (5502), and the enlargement incision part (550*a*) enlarges the incised portion in the Z axis direction by the channel extension surface (5513) at the connection portion (5503).

At that time, at a whole section of the enlargement incision part (550*a*), an overall skin incision line is formed through the outside edge line (5516), and this is formed in a form of being continuously changed in the Y axis and Z axis directions from the dot point tip (5514) and being enlargedly incised. After that, because the insertion support part (550*b*) is inserted into the skin along the incised line, skin pain may not be almost felt during the insertion process of the insertion support part (550*b*).

Accordingly, because the insertion guide needle (550) according to one embodiment of the present disclosure incises the skin and continuously enlarges the incised portion through the enlargement incision part (550*a*) having the dot point tip (5514) of a point-contact structure during the skin incision process, the skin pain can be minimized, as the enlargement incision direction of the enlargement incision part (550*a*) is continuously changed and enlarged to the Z axis direction after the Y axis direction enlargement through the point top portion (5501), the skin pain can be minimized during the enlargement incision process, and by continuously inserting the insertion support part (550*b*) along the incised line of the enlargement incision part (550*a*), skin pain may not be almost felt during the insertion process of the insertion support part (550*b*).

FIG. 8 is a flowchart for illustrating a method for manufacturing an insertion guide needle according to operation flow step by step according to an embodiment of the present disclosure, and FIGS. 9 to 11 are figures for illustrating a method for manufacturing an insertion guide needle according to an embodiment of the present disclosure.

A method for manufacturing an insertion guide needle according to an embodiment of the present disclosure is related to a method for manufacturing the insertion guide needle (550) of the structure described above, and comprises a step (S10) for preparing a needle original plate (5500) of metallic material lengthily formed along the body insertion direction, a step (S20) for cutting a front end portion of the needle original plate (5500) so that the enlargement incision part (550*a*) configured to enlarge an incised portion of the skin of the human body as the insertion guide needle (550) is being inserting into the human body can be formed, and a step (S30) for bending both side end portion in a width direction with respect to the cut needle original plate (5500).

The step (S20) for cutting the front end portion of the needle original plate (5500) is performed in a way of cutting the needle original plate (5500) to form the dot point tip (5514) of a structure in which the front end portion of the enlargement incision part (550*a*) point-contacts the skin of the human body.

More specifically, the step (S20) for cutting the front end portion of the needle original plate (5500) is performed in ways of firstly first-cutting the needle original plate (5500) by a cutting knife blade (KN) to form the first slated surface (5521) in a direction of crossing a length direction center axis (X axis) passing the upper side of the needle plate (5500) as illustrated in FIG. 9, and, in this state, second-cutting the needle original plate (5500) by the cutting knife blade (KN) so that the second slanted surface (5522) is formed symmetrically with the first slated surface (5521) with respect to the length direction center axis (X axis) of the needle original plate (5500) as illustrated in FIG. 10.

At that time, it is performed so that the first slated surface (5521) and the second slanted surface (5522) are formed to be slanted in a direction away from the virtual plane (VP) (See FIG. 5) including the length direction center axis (X axis) and the dot point tip (5514) as going down to the bottom portion.

Additionally, it is performed so that one cross point (CP) crossing the first and second slanted surfaces (5521, 5522) and the length direction center axis (X axis) with each other is located at a position spaced apart from the front end portion of the needle original plate (5500) at a certain distance.

Further, it is performed so that the first slated surface (5521) and the second slanted surface (5522) are crossed symmetrically with each other with respect to the length direction center axis (X axis) of the needle original plate (5500) as a center, the point tip edge line (5515) (See FIG. 5) is formed along the crossing line, and the dot point tip (5514) is formed at the front end portion of the point tip edge line (5515). The point tip edge line (5515) is formed on the virtual plane (VP) described above and formed in a structure of being upwardly slanted as being toward the back.

By forming the first slated surface (5521) and the second slanted surface (5522) by cutting in this way, the enlargement incision part (550*a*) is formed, the point tip edge line (5515) is formed on a line crossing the first slated surface (5521) and the second slanted surface (5522), and the dot point tip (5514) configured to be point-contactable with the skin is formed at the front end portion of the point tip edge line (5515).

After forming the first slanted surface (5521) and the second slanted surface (5522) at the front end portion of the needle original plate (5500) through this cut process, both side end portions of the need original plate (5500) with respect to the width direction are bent along bending lines (BL) as illustrated in FIG. 11, and this can be performed through a press forming processing according to an embodiment of the present disclosure.

At that time, the bending process of the needle original plate (5500) is performed by sequentially forming the point tip portion (5501), the variation portion (5502) and the connection portion (5503) (See FIG. 5) described above at the enlargement incision part (550a) from the front end portion to the back side.

As described above, the point tip portion (5501) is gradually enlarged in the width direction of the needle original plate (5500) (Y axis direction) from the dot point tip (5514) toward the back and therefore is formed to incise the skin of the human body and enlarge the incised portion in the corresponding direction during the body insertion process, the structure of the variation portion (5502) is changed to be firstly enlarged in the width direction of the needle original plate (5500) (Y axis direction) and then be enlarged in the thickness direction (Z axis direction) as being toward the back, thereby incising the skin of the human body and enlarging the incised portion in the corresponding direction (Y axis direction and Z axis direction) during the body insertion process, and the connection portion (5503) is enlarged in the thickness direction of the needle original plate (5500) as being toward the back, thereby incising the skin of the human body and enlarging the incised portion in the corresponding directions during the body insertion process.

The detailed descriptions regarding them are the same or similar to the description described above with respect to FIGS. 4 to 7, and therefore those are omitted to prevent duplicate description.

The insertion guide needle (550) according to an embodiment of the present disclosure can be easily manufactured through those cut processing and bending processing, the enlargement incision part (550a) and other elements continuously incising the skin and enlarging the incised portion can be conveniently manufactured through those simple processing processes, and through this the manufacturing cost can be reduced as well as the precision of the size of the insertion guide needle can be improved.

The foregoing descriptions have been presented in order to explain certain principles of the present disclosure by way of example, and a person having ordinary skill in the art which the present disclosure relates could make various modifications and variations without departing from the essential features of the present disclosure. Accordingly, the foregoing embodiments disclosed in the present disclosure shall be interpreted as being illustrative, while not being limitative, of the principle and scope of the present disclosure. It should be understood that the scope of the present disclosure shall be defined by the Claims and all of their equivalents fall within the scope of the present disclosure.

What is claimed is:

1. An insertion guide needle for a continuous blood glucose monitoring device, which is configured to be inserted into a body together with a sensor unit to guide body insertion of the sensor unit and being extracted and removed from the body after insertion, the insertion guide needle comprising:
   an enlargement incision part formed at a front end portion of the insertion guide needle to enlarge an incised portion of skin of the body in a process of being inserted into the body; and
   an insertion support part formed to extend at a back end portion of the enlargement incision part in a direction of a first axis to be continuously inserted into the body along the incised portion enlarged by the enlargement incision part,
   wherein the enlargement incision part is formed to have a dot point tip of a structure of point-contacting with the skin of the body when a front end portion of the enlargement incision part is being inserted into the body,
   wherein the enlargement incision part comprises:
   a point tip portion configured to enlarge the incised portion of the skin of the body in a direction of a second axis as being from the dot point tip to a back of the insertion guide needle;
   a connection portion configured to enlarge the incised portion of the skin of the body in a direction of a third axis as being toward the back of the insertion guide needle, wherein a back end of the connection portion is connected with the insertion support part; and
   a variation portion disposed between the point tip portion and the connection portion, and configured to enlarge the incised portion of the skin of the body by changing an enlargement incision direction from the direction of the second axis to the direction of the third axis as being toward the back of the insertion guide needle,
   wherein the point tip portion comprises:
   a first portion extended from the dot point tip in the direction of the first axis, and configured to enlarge the incised portion of the skin of the body in the direction of the second axis and in the direction of the third axis as being toward the back of the insertion guide needle, and
   a second portion extended from the first portion in the direction of the first axis to be connected to the variation portion, and configured to enlarge the incised portion of the skin of the body only in the direction of the second axis as being toward the back of the insertion guide needle.

2. The insertion guide needle for the continuous blood glucose monitoring device according to claim 1,
   wherein the insertion support part
   is lengthily formed to have a length component along a-the first axis of a front-back direction parallel to a direction of the body insertion, and forms an inner receivable space and has a structure of including a whole one side opened along a-the direction of the first axis, wherein, among the second axis of a width direction perpendicular to the first axis and a-the third axis of a height direction, the one side crosses with the third axis.

3. The insertion guide needle for the continuous blood glucose monitoring device according to claim 1,
   wherein the point tip portion comprises slanted enlargement surfaces formed to be enlarged in the direction of the second axis as being from the dot point tip toward the back of the insertion guide needle, the slanted enlargement surfaces are formed along the direction of the second axis at both sides with respect to the dot point tip, and the slanted enlargement surfaces are formed to be slanted in a direction of being away from a virtual plane comprising the dot point tip and the first axis as being toward a bottom of the insertion guide needle.

4. The insertion guide needle for the continuous blood glucose monitoring device according to claim 3, wherein a point tip edge line is formed by crossing the slanted enlargement surfaces formed at the both sides of the dot point tip with each other with respect to the dot point tip, and the point tip edge line is formed on the virtual plane comprising the dot point tip and the first axis and is formed to have a structure of upwardly slated as being from the dot point tip to the back of the insertion guide needle.

5. The insertion guide needle for the continuous blood glucose monitoring device according to claim 3, wherein the variation portion comprises variation extension surfaces forming a same plane as the slanted enlargement surfaces at a front end of the variation extension surfaces and extended in the directions of the second axis and the third axis in a structure of continuously changing a direction of which variation extension surfaces face as being toward the back of the insertion guide needle.

6. The insertion guide needle for the continuous blood glucose monitoring device according to claim 5, wherein a surface of a back end of the variation extension surfaces is formed to be slanted in a direction in which a perpendicular upwardly extended from the surface of the back end of the variation extension surfaces is crossed with the virtual plane including the dot point tip and the first axis.

7. The insertion guide needle for the continuous blood glucose monitoring device according to claim 5, wherein the connection portion comprises channel extension surfaces forming a same plane as the variation extension surfaces at a front end of the channel extension surfaces and extended in the direction of the third axis as being toward the back of the insertion guide needle.

8. The insertion guide needle for the continuous blood glucose monitoring device according to claim 7, wherein a whole area of the channel extension surfaces is formed to be slanted in a direction in which a perpendicular upwardly extended from the whole area of the channel extension surfaces is crossed with the virtual plane including the dot point tip and the first axis.

9. The insertion guide needle for the continuous blood glucose monitoring device according to claim 1, wherein the insertion support part is formed in a shape in which both side end portions in a width direction of the insertion support part are upwardly bent with respect to a plate lengthily formed to have a length component along a front-back direction.

\* \* \* \* \*